United States Patent [19]

Jett et al.

[11] Patent Number: 5,405,747
[45] Date of Patent: Apr. 11, 1995

[54] METHOD FOR RAPID BASE SEQUENCING IN DNA AND RNA WITH TWO BASE LABELING

[75] Inventors: James H. Jett; Richard A. Keller; John C. Martin; Richard G. Posner; Babetta L. Marrone; Mark L. Hammond; Daniel J. Simpson, all of Los Alamos, N. Mex.

[73] Assignee: The Regents of the University of California Office of Technology Transfer, Alameda, Calif.

[21] Appl. No.: 208,506

[22] Filed: Mar. 7, 1994

Related U.S. Application Data

[63] Continuation of Ser. No. 765,277, Sep. 25, 1991, abandoned.

[51] Int. Cl.$^6$ .................... C12Q 1/68; C12P 19/34; G01N 33/48
[52] U.S. Cl. ..................... 435/6; 435/91.1; 436/94
[58] Field of Search ............... 435/6, 91.1; 436/94

[56] References Cited

U.S. PATENT DOCUMENTS 4,962,037  10/1990  Jett et al. .................... 435/6
4,962,045  10/1990  Picozza et al. .................... 436/501

OTHER PUBLICATIONS

L. M. Smith et al., "Fluorescence Detection in Automated DNA Sequence Analysis," Nature 321, 674 (1986).

James M. Prober et al., "A System for Rapid DNA Sequencing with Fluorescent Chain-Terminating Dideoxynucleotides," Science 238, 336 (1987).

James H. Jett et al., "High-Speed DNA Sequencing: An Approach Based Upon Fluorescence Detection of Single Molecules," J. Biomolecular Struc. & Dynamics 7, 301 (1989).

Harding et al., *Trends in Biotech.* 10, 55-57 (1992).

Primary Examiner—Margaret Parr
Assistant Examiner—Kenneth R. Horlick
Attorney, Agent, or Firm—Samuel M. Freund

[57] ABSTRACT

Method for rapid-base sequencing in DNA and RNA with two-base labeling and employing fluorescent detection of single molecules at two wavelengths. Bases modified to accept fluorescent labels are used to replicate a single DNA or RNA strand to be sequenced. The bases are then sequentially cleaved from the replicated strand, excited with a chosen spectrum of electromagnetic radiation, and the fluorescence from individual, tagged bases detected in the order of cleavage from the strand.

60 Claims, 4 Drawing Sheets

Rhodamine-6-dATP

Rhodamine-6-dCTP

Fluorescein-7-dUTP

*Fig. 3a*

5-(3-aminoallyl)dCTP 5-(3-aminopropynyl)dCTP 5-(3-aminoallyl)dUTP

Amino-6-dCTP

*Fig. 3b*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 10 bases
( B ) TYPE: nucleic acid
( C ) STRANDEDNESS: single
( D ) TOPOLOGY: linear ( x i ) SEQUENCE DESCRIPTION: SEQ ID NO: 1:

AATGGCACTG   10

METHOD FOR RAPID BASE SEQUENCING IN DNA AND RNA WITH TWO BASE LABELING

BACKGROUND OF THE INVENTION

The present invention is the result of research conducted with U.S. Government support under Contract No. W-7405-ENG-36 between the Department of Energy and the Regents of the University of California. The Government has certain rights in this invention.

This is a continuation of application Ser. No. 07/765,277 filed on Sep. 25, 1991, now abandoned.

The invention is related generally to DNA and RNA sequencing and, more particularly, to DNA and RNA sequencing by the detection of individual nucleotides specifically labeled with fluorescent dyes and excited using electromagnetic radiation.

The subject of analyzing the base sequence of DNA and/or RNA has received world-wide attention as is stated in U.S. Pat. No. 4,962,037 for "Method Far Rapid Base Sequencing In DNA And RNA," issued to James H Jett et al. on Oct. 9, 1990, which is hereby incorporated by reference herein. Therein, the inventors teach the enzymatic synthesis of a complementary strand of DNA or RNA to be sequenced from bases having identifiable characteristics and thereafter sequencing the complementary strand. A fluorescent dye is attached to each base before the synthesis step, and the resulting modified DNA or RNA strand is sequentially cleaved to release the modified bases, one at a time. The freed bases are then detected by observing the fluorescence from the individually excited bases.

In view of the molecular weight, steric bulk, and interactions of dyes which provide significant fluorescent yields, special enzymes may have to be employed for use in the complementary replication step, and special exonucleases may have to be developed to achieve the sequential cleavage step. Moreover, the complexity of the replication and cleavage reactions may result in poor fidelity of insertion and release of the modified nucleotides, respectively. If the dye labeling of the bases, or a portion thereof, could be achieved after the sequential cleavage of the complementary strand by use of relatively small reactive centers installed on the bases used in the replication process, or a fewer number of bases would be required to be labeled in each complementary strand, the replication process could be made simpler and potentially more accurate.

Accordingly, it is an object of the present invention to reduce the steric extent of the modifications to bases used in the replication of the DNA or RNA strands to be sequenced.

Another object of the present invention is to reduce the number of bases which are required to be modified for use in the replication of the DNA or RNA strands to be sequenced.

Additional objects, advantages and novel features of the invention will be set forth in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purposes of the present invention, as embodied and broadly described herein, the method for base sequencing DNA and RNA includes the steps of isolating a single fragment of the DNA or RNA; enzymatically synthesizing a strand of DNA or RNA complementary to the single fragment of DNA or RNA to be sequenced using bases selected from the group of four bases found in DNA and RNA, a chosen first base being modified in a manner characteristic of that base, while the remaining three bases are modified identically; sequentially cleaving the end base from the DNA or RNA strand forming thereby a train of modified bases, adding a fluorescent tag to each modified base appropriate to the modification of that base prior to the replication step, post replication, but pre-cleavage, or post-cleavage, or in a combination thereof; exciting each tagged base using a chosen spectrum of electromagnetic radiation; and detecting the fluorescence characteristic of the chosen base and that of the three remaining bases in the train in sequential passage through a detector which detects the fluorescence from single molecules, whereby the first chosen base and the three remaining bases can be distinguished. Preferably, the above steps are repeated an additional two times for a total of three complete sequencing operations, in each repetition, a different first base being chosen, so that the DNA or RNA base sequence is obtained.

In a further aspect of the present invention, in accordance with its objects and purposes, the method for base sequencing DNA and RNA includes the steps of isolating a single fragment of the DNA or RNA; enzymatically synthesizing a strand of DNA or RNA complementary to the single fragment of DNA or RNA to be sequenced using bases selected from the group of four bases found in DNA and RNA, a chosen first base being modified in a manner characteristic of that base, while a chosen second base is modified in a manner characteristic of that base; sequentially cleaving the end base from the DNA or RNA strand forming thereby a train of bases, some of which are modified; adding a fluorescent tag to each modified base appropriate to the modification of that base prior to the replication step, post replication, but pre-cleavage, or post-cleavage, or in a combination thereof; exciting each tagged base using a chosen spectrum of electromagnetic radiation; and detecting the fluorescence characteristic of the chosen first base and that of the chosen second base in the train in sequential passage through a detector which detects the fluorescence from single molecules, whereby the chosen first base and the chosen second base can be distinguished. Preferably, the steps are repeated five additional times for a total of six complete sequencing operations, in each repetition, a different combination of first and second base being chosen, so that the DNA or RNA base sequence is obtained.

Benefits and advantages of the present invention include significant simplification of the detection process, since only two wavelengths need be detected. In the situation where the fluorescent tags are placed on the bases post-replication, or post-cleavage, or in the second method, where only two bases are tagged, the crowding in the replicated molecule is reduced, thereby allowing for more facile replication and cleavage steps, and a reduction in the possibility of flawed DNA or RNA replication.

BRIEF DESCRIPTION OF THE DRAWINGS

The accompanying drawings, which are incorporated in and form a part of the specification, illustrate several embodiments of the present invention and, together with the description, serve to explain the principles of the invention. In the drawings:

FIG. 3a illustrates two fluorescent dyes attached through linker groups to three different bases and suitable for incorporation into the complementary DNA or RNA strand during the replication process. While

DETAILED DESCRIPTION OF THE PREFERRED EMBODIMENT OF THE INVENTION

Briefly, the method according to the present invention for base sequencing DNA and RNA employs fluorescent detection of single molecules at two wavelengths. In a first embodiment of the invention, a strand of DNA or RNA complementary to the single fragment of DNA or RNA to be sequenced is synthesized using bases selected from the group of four bases found in DNA and RNA. A chosen first base is modified in a manner characteristic for that base, while the remaining three bases are modified identically. The end bases are sequentially cleaved from the DNA or RNA strand and formed into a train of modified bases. A fluorescent tag is added to each modified base appropriate to the modification of that base either prior to the replication step, post-replication, but pre-cleavage, or post-cleavage, or in a combination thereof. The tagged bases are then individually excited using a chosen spectrum of electromagnetic radiation. The fluorescence therefrom is detected as the bases pass in sequence through a detector which detects the fluorescence from single molecules, whereby the first chosen base and the three remaining bases can be distinguished. Repeating the above steps two additional times for a total of three complete sequencing operations, in each repetition, a different first base being chosen, allows the complete DNA or RNA base sequence to be obtained.

In a second embodiment, only two bases are labeled. Fluorescent dyes are added to the modified bases again either prior to the replication step, post-replication, but pre-cleavage, or post-cleavage, or a combination thereof, and the steps are similar to those set forth above. These steps are repeated five additional times for a total of six complete sequencing operations, in each repetition, a different combination of first and second bases being chosen, in order that the complete DNA or RNA base sequence can be obtained.

Reference will now be made in detail to the present preferred embodiments of the invention, examples of which are illustrated in the accompanying drawings. Turning first to the embodiment where one nucleotide is tagged with one fluorescent dye, while those remaining nucleotides are tagged with another fluorescent dye which fluoresces at a different wavelength than the first dye. Using only two dyes has a definite detection advantage over labeling all bases with dyes which fluoresce at distinctly different (4) wavelengths, and is in contrast with the teachings of the Jett et al. patent, supra, each base type is labeled with a different fluorescent dye. However, the number of sequencing steps is increased using the present invention. The tagging or labeling process can be achieved as part of one or two of the sequencing steps. These steps include the enzymatic replication of the DNA or RNA strand to be sequenced, after the strand is isolated. The replication step is performed using bases which have been modified. A first base is chosen for unique labeling from the remaining three bases found in DNA and RNA. Fluorescent dye tag(s) can be introduced onto all of the bases at this point or onto only the chosen first base or onto only the remaining three bases. A disadvantage of placing the fluorescent dye molecules onto the bases at this point is the possible steric hindrance among these large molecules, This may increase the difficulty of attaining completeness and accuracy of replication and locating the appropriate enzymes to enable the replication and subsequent cleavage steps to take place. Some relief from steric effects may be obtained by using "linker arms" between the base and the fluorescent dye labels as will be more fully described below.

Another procedure is to tag each base with a reactive site, perhaps using a linker arm. Such reactive sites may include amino groups ($-NH_2$) or sulfhydro groups ($-SH$). The steric problem is thereby significantly reduced. The dye labels may be added in part or in full before the replication step, after the replication step, but before the cleavage step, or after the cleavage step, if reactive sites are employed in the modification of some or all of the nucleotides. After the replication step, the nucleotides are sequentially cleaved from the end of the replicated DNA or RNA strand using an exonuclease, and the fragments are introduced into a flowing fluid stream in the order of detachment from the strand. See, e.g., the Jett et al. patent, supra. As mentioned above, the dyes may be added to the modified bases at this point. The fully tagged bases are then excited using a chosen wavelength of electromagnetic radiation, and passed through a detector suitable for detecting fluorescence from single molecules. See, e.g., L. M. Smith et al., "Fluorescence Detection in Automated DNA Sequence Analysis," Nature 321, 674 (1986); J. N. Proher et al., "A System for Rapid DNA Sequencing with Chain-Terminating Dideoxynucleotides," Science 238, 336 (1987); and J. H. Jett et al., "High Speed DNA Sequencing: An Approach Based Upon Fluorescence Detection Of Single Molecules, " J Biomolecular Struc. & Dynamics 7, 301 (1989).

The information provided in a sequencing run will be the number of nucleotides between each uniquely labeled nucleotide. By repeating the process two additional times with the unique dye on a different nucleotide each time, sequencing can be achieved as follows. Consider the hypothetical sequence (SEQ ID NO. 1) AATGGCACTG 1. First label the T's red and the remaining bases green. The detected bases are then in the order, green, green, red, green, green, green, green, green, red, green. The third and ninth bases are T's.
2. Next label the G's red and the remaining bases green. The detected bases are now in the order, green, green, green, red, red, green, green, green, green, red. The fourth and tenth are G's.
3. Finally, label the A's red and the remaining bases green. The detected bases are in the order, red, red, green, green, green, green, red, green, green, green; and the first, second, and seventh are A's.

The sixth and eighth bases must then be C's. Here T is thymine, A is adenins, G is guanine, and C is cytosine.

Figure 1:
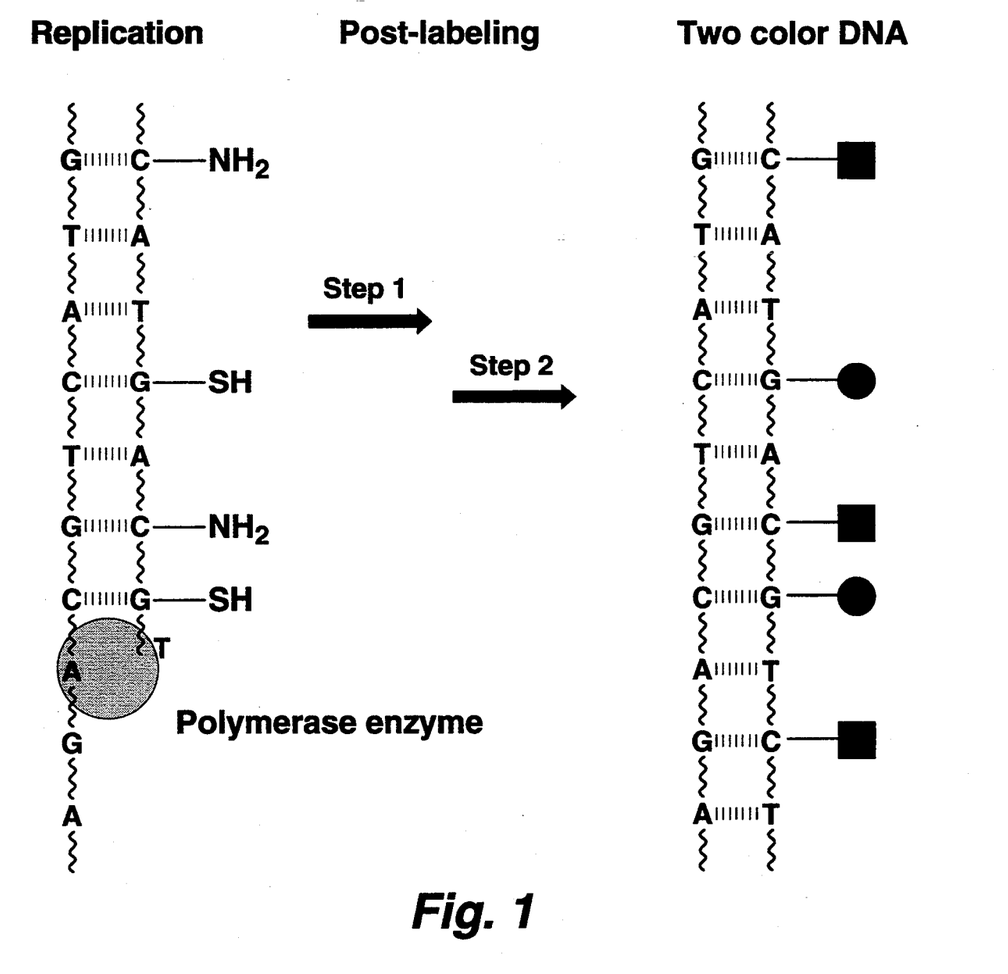
FIG. 1 is a schematic representation of the placement of reactive center onto two of the bases used to replicate the DNA or RNA strand to be sequenced, followed by the introduction of the dye molecules onto the already modified bases, all prior to the sequential cleavage steps.
Figure 2:
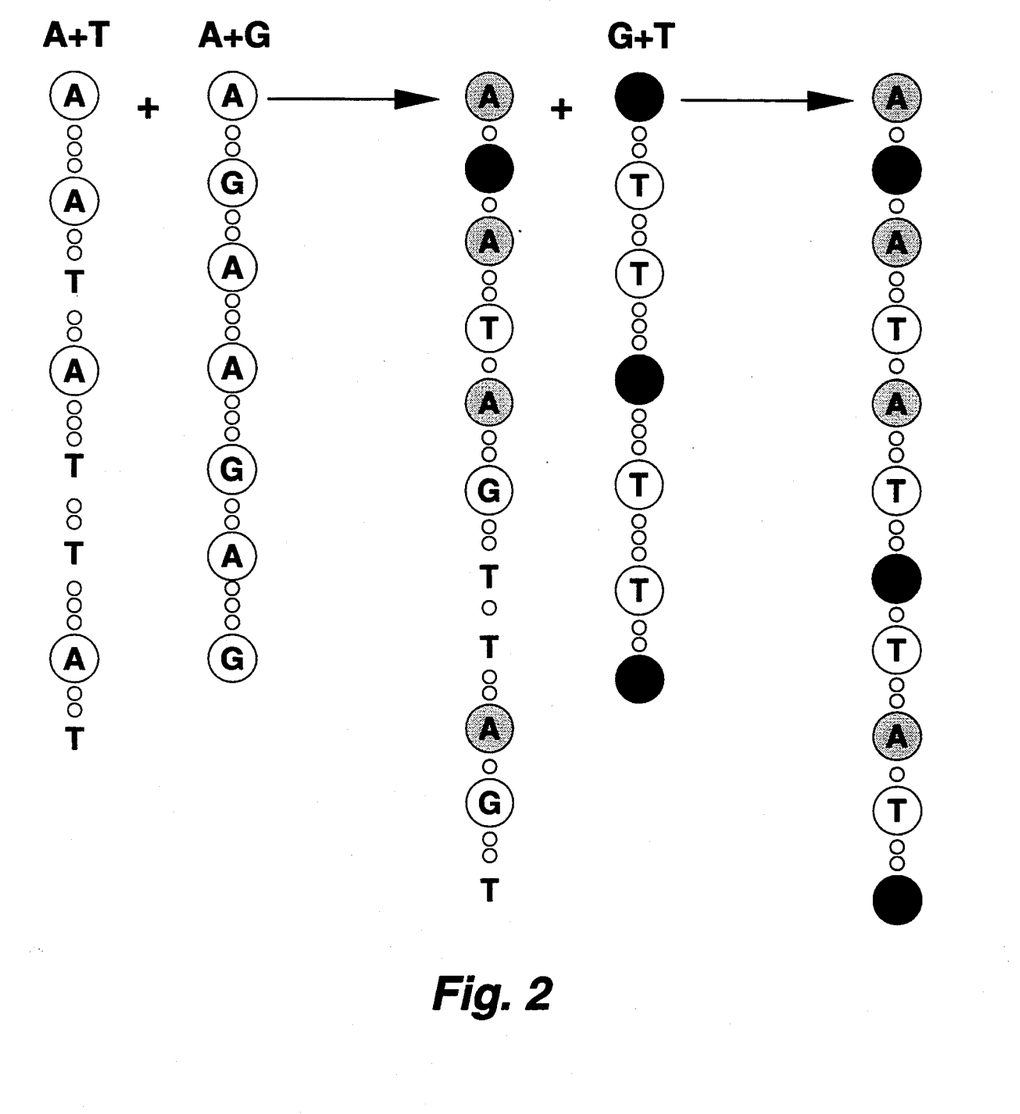
FIG. 2 is a schematic representation of the two-base sequencing procedure shown in FIG. 1 hereof illustrating the number of base-pair sequences which must be investigated in order to unequivocally establish the correct overall sequence. For three bases, three sequences of two bases each are required.

Sequencing DNA and RNA strands with single-molecule detection techniques by labeling only two of the four bases and detecting the two base-specific labels in multiple runs is also possible. Here the steric hindrance is further reduced, while the detection advantage is maintained. For example, if A and C are labeled and detected in an apparatus, then the order and numbers of A's and C's will be known. If the next data set is obtained from a strand with the A's and T's labeled, the two data sets can be combined to produce a sequence A, T and C. However, there will be ambiguities in the order of adjacent C's and T's. These ambiguities can be removed by reading a strand with the C's and T's labeled. At this point, the combined sequence of A's, C's and T's is complete and correct. FIGS. 1 and 2 graphically illustrate the process. In step 1 of FIG. 1, the three modified bases used in the replication step contain reactive centers. In step 2 thereof, the fluorescent dyes are attached to the reactive centers and the DNA strand is ready for the sequential cleavage step.

Placing the fourth base, G, in the sequence will require information from three data sets in which the G's are labeled along with each of the other bases. Once that information is obtained, it is possible to reconstruct the whole, complete sequence. Thus, to reconstruct the complete four-base sequence, it is necessary to record data on each of the six possible combinations of labeled bases when only two bases are labeled at a time.

The Table clarifies the relationship among the subject claims and the step at which the fluorescent dye is added to the bases to be sequenced for the two-color, four-base labeling procedure (#1), and for the two-color, two-base labeling procedure (#2).

A similar scheme could be constructed for labeling of three bases at a time which would increase the hindrance

TABLE

| Claim No. | Procedure No. | Type of Labeling |
|---|---|---|
| 1 | 1 | all pre-replication |
| 6 | 1 | all post-cleavage |
| 11 | 1 | pre-replication; 3 post-cleavage |
| 16 | 1 | 3 pre-replication; 1 post-cleavage |
| 36 | 1 | all post-replication |
| 41 | 1 | 1 pre-replication; 3 pre-cleavage |
| 46 | 1 | 1 pre-cleavage; 3 pre-replication |
| 66 | 1 | 1 pre-cleavage; 3 post-cleavage |
| 71 | 1 | 1 post-cleavage; 3 pre-cleavage |
| 21 | 2 | both pre-replication |
| 26 | 2 | both post-cleavage |
| 31 | 2 | 1 pre-replication; 1 post-cleavage |
| 51 | 2 | both pre-cleavage |
| 56 | 2 | 1 pre-replication; 1 pre-cleavage |
| 61 | 2 | 1 pre-cleavage; 1 post-cleavage | difficulties, while decreasing the overall number sequencing steps.

Having generally described the invention, the specific embodiments thereof are illustrated by the following examples.

Example I

DNA strands up to 500 nucleotides in length containing one fluorescent nucleotide and three normal nucleotides have been synthesized. The DNA synthesis was observed by modified T7 DNA polymerass (Sequence Version 2.0 from United States Biochemicals) with rhodamine-dCTP, rhodamine-dATP, rhodamine-dUTP, fluorescein-dATP, and fluorescein-dUTP. DNA synthesis has also been observed by modified T5 DNA polymerase (Life Technologies, Inc.) with rhodamine-dCTP and rhodamine-dATP.

Example II

DNA substrates containing one fluorescent nucleotide (rhodamine-dCTP or fluorescein-duTP) and three normal nucleotides have been successfully digested by six different enzymes: native T4 polymerase, native T7 polymerass, Klenow fragment of E. coli pol I, Exo III, E. coli pol III holoenzyme, and snake venom phosphodiesterase.

Native T7 polymerass digests DNA containing rhodamine-dCTP at a rate of 5–10 nucleotides/see, DNA Containing fluorescein-dATP at 5–50 nucleotides/see, and DNA with all four normal nucleotides at −30 nucleotides/sec.

Example III

Incorporation of 5-(3-aminopropynyl)-dCTP, 5-(3-aminoallyl)-dCTP and 5-(3-aminoallyl)-dUTP individually into M13 DNA and observed full-length replication (7250 bp) at rates on the order of those of normal nucleotides has been observed. Replication was verified by gel electrophoresis.

A large scale M13 (5-(3-aminopropynyl)-dCTP incorporated) preparation was made and purified by phenol/chloroform extraction, ethanol precipitation and spin-column chromatography. The purified DNA (15 μg/reaction) was post-labeled by treatment with excess (10 mg/mL) 5-(and -6)-carboxytetramethylrhodamine, succinimidyl ester (TMR-NHS) at two different temperatures in two different buffers. Condition A: Bicarbonate buffer, pH 8.2 at 25° C. and 65° C. Condition B: Borate buffer, pH 9.1 also at 25° C. and 65° C. All four reactions were incubated for four hours. The labeled DNA was purified by ethanol precipitation and by further ringing with 70% ethanol. The yield of DNA obtained from post-labeling was quantitated by HPLC with absorbance detection at 260 nm using standards of modified, unlabeled M13. Separation was performed on a Waters Gen-pak FAX column eluting with a gradient of 0.3–1M NaCl in a background buffer of 25 mM Tris/1 mM EDTA. Fractions slutlug (19–21 min) in the size area expected for M13 showed both absorbance at 260 nm and fluorescence excitation and emission characteristic of tetramethylrhodamine. Material was collected from the HPLC and tetramethylrhodamine concentration was determined on the spectrofluorometer. The extent of labeling, approximately 2% of the possible 1812 sites, was determined from HPLC peak area (260 nm) and fluorescence emission measurement versus TMR-NHS standards. No significant differences were observed in post-labeling efficiency under any of the conditions examined thus far.

Figure 3A:
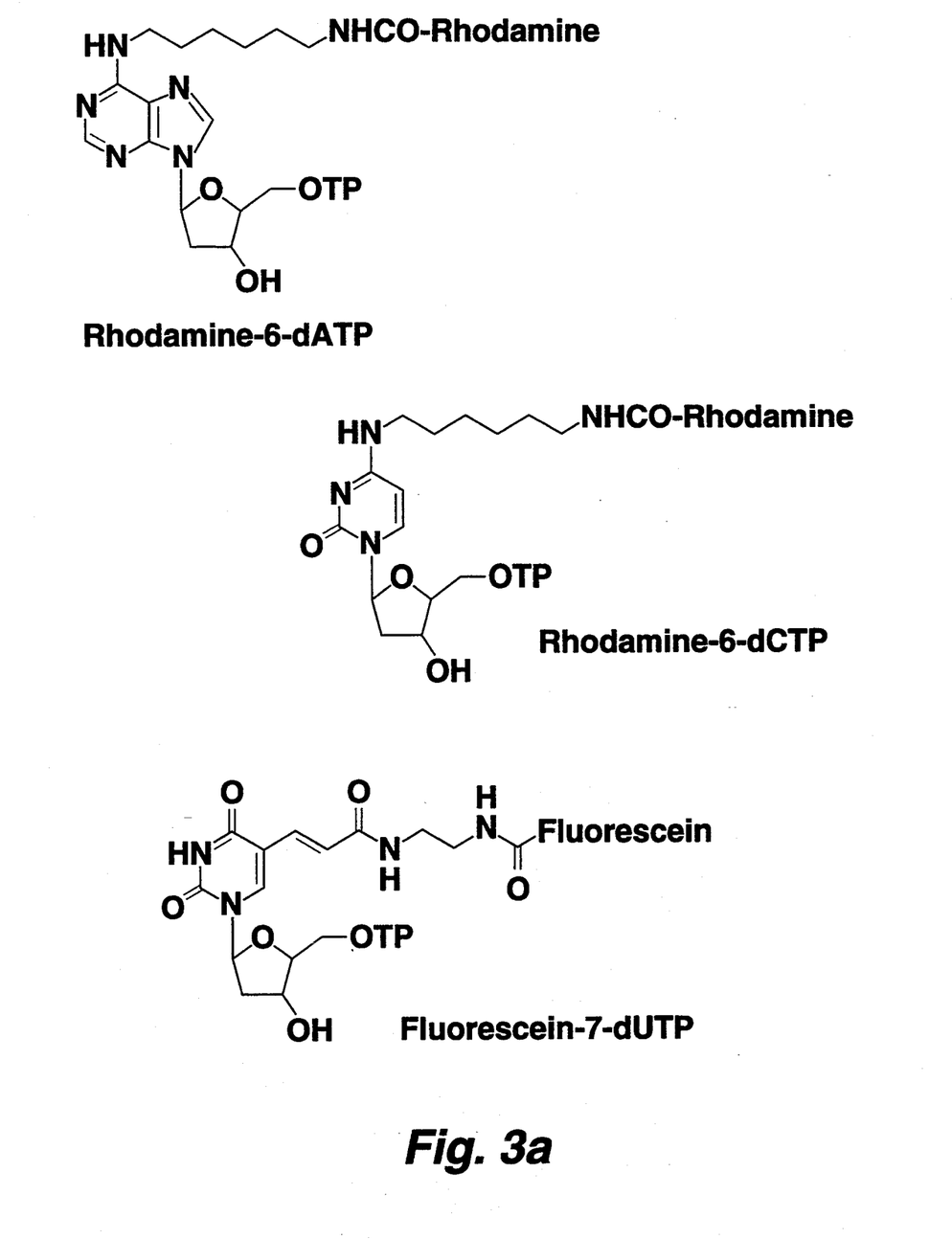
Figure 3B:
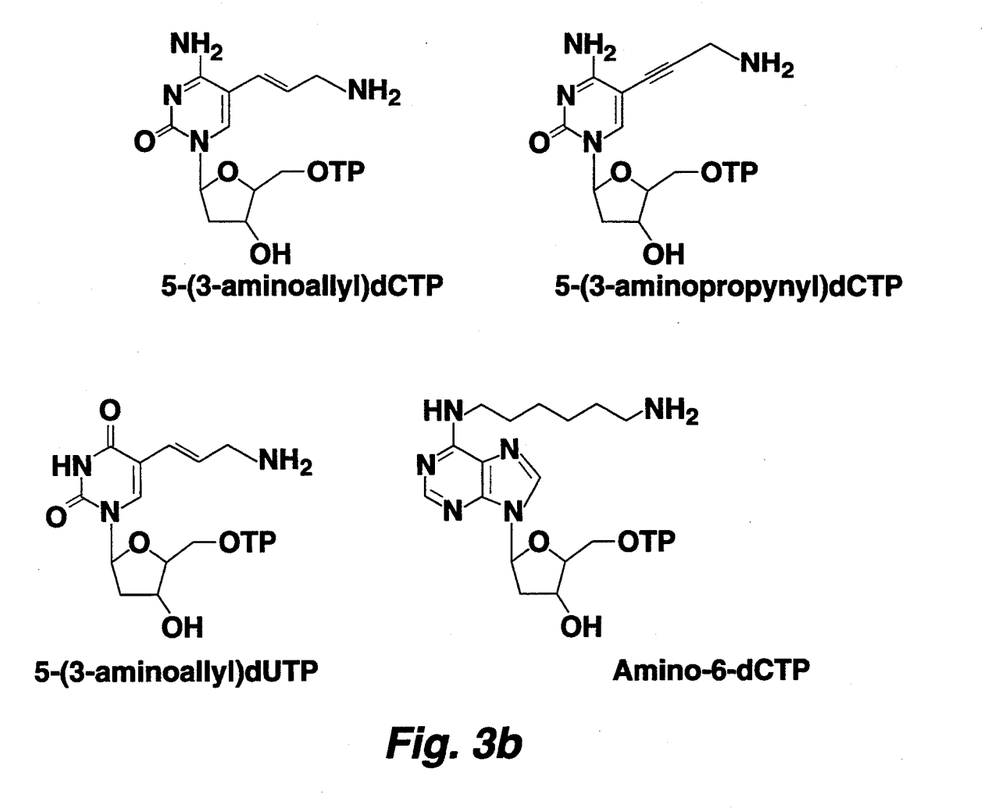
FIG. 3b illustrates reactive centers in the form of amino-groups attached to two different bases through a sampling of linker groups suitable for incorporation into the DNA or RNA strand during the replication process, for post-replication labeling with fluorescent dyes.

Two fluorescent dyes attached through linker groups to three different bases and suitable for incorporation into the complementary DNA or RNA errand during the replication process are illustrated in FIG. 3a, while FIG. 3b illustrates reactive centers in the form of amino-groups attached to two different bases through a sampling of linker groups suitable for incorporation into the DNA or RNA strand during the replication process, for post-replication labeling with fluorescent dyes.

The foregoing description of the preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

oresces to fluoresce at a second wavelength of light characteristic of the remaining modified bases when excited using the chosen electromagnetic radiation;
(c) attaching said synthesized complementary strand to a microsphere and suspending said microsphere in a laminar flow fluid stream
(d) sequentially cleaving the end base from the DNA or RNA fragment to form a train of modified bases in said stream;
(e) exciting each modified base in the train of modified bases with the chosen electromagnetic radiation; and
(f) detecting the fluorescence at either the first wavelength of light or at the second wavelength of light for each modified base in the train in sequential passage through a detector which detects the fluorescence from single molecules wherein said step of detecting provides information on the nucleotide sequence of said single fragment of DNA or RNA to be sequenced.

2. The method as described in claim 1, wherein said step of sequentially cleaving the end base from the DNA or RNA is achieved using exonuclease.

3. The method as described in claim 1, wherein said steps (a) through (f) are sequentially repeated two additional times using identical single fragments of DNA or RNA, whereby in each completed sequence of steps a different first base is chosen for modification such that the chosen first base fluoresces at a different first wavelength of light than the second wavelength of fluorescence of the remaining three bases when the modified bases are sequentially excited by the chosen electromagnetic radiation.

---

What is claimed is:

1. A method for DNA and RNA nucleotide base sequencing comprising the steps of:
    (a) isolating a single fragment of DNA or RNA;
    (b) enzymatically synthesizing a strand of DNA or RNA complementary to the single fragment of DNA or RNA to be sequenced using nucleotide bases modified such that a chosen first base selected from the group consisting of the four bases found in DNA or RNA is modified by attachment of a first fluorescent dye which fluoresces at a first wavelength of light characteristic of the first modified base when excited using a chosen spectrum of electromagnetic radiation, while the remaining three bases found in DNA or RNA are each modified by attachment of a second fluorescent dye which flu- 4. The method as described in claim 1, wherein the chosen first base and the remaining three bases are modified by attach fluorescent dyes which are separated from the base using a linker arm in order to assist in the synthesis and cleavage of the complementary strand of DNA or RNA.

5. A method for DNA and RNA nucleotide base sequencing comprising the steps of:
    (a) isolating a single fragment of DNA or RNA;
    (b) enzymatically synthesizing a strand of DNA or RNA complementary to the single fragment of DNA or RNA to be sequenced using nucleotide bases modified such that a chosen first base selected from the group consisting of the four bases found in DNA or RNA is modified to have a first reactive center selected from the group consisting of amino and sulfhydro groups, while the remaining three bases found in DNA or RNA are each modified to have a second reactive center selected from the group consisting of amino and sulfhydro groups;

(c) attaching said synthesized complementary strand to a microsphere and suspending said microsphere in a laminar flow fluid stream;

(d) sequentially cleaving the end base from the DNA or RNA fragment to form a train of modified bases in said stream;

(e) attaching a first fluorescent dye to each first reactive center and a second fluorescent dye to each second reactive center, such that the first fluorescent dye fluoresces at a first wavelength of light characteristic of the first modified base when excited using a chosen spectrum of electromagnetic radiation, and the second fluorescent dye fluoresces at a second wavelength of light characteristic of the remaining three bases found in DNA or RNA when excited using the chosen electromagnetic radiation;

(f) exciting each modified base in the train of modified bases with the chosen electromagnetic radiation; and (g) detecting the fluorescence at either the first wavelength of light or at the second wavelength of light for each modified base in the train in sequential passage through a detector which detects the fluorescence from single molecules wherein said step of detecting provides information on the nucleotide sequence of said single fragment of DNA or RNA to be sequenced.

6. The method as described in claim 5, wherein said step of sequentially cleaving the end base from the DNA or RNA is achieved using exonuclease.

7. The method as described in claim 5, wherein said steps (a) through (g) are sequentially repeated two additional times using identical single fragments of DNA or RNA, whereby in each completed sequence of steps a different first base is chosen for modification such that the chosen first base fluoresces at a different first wavelength of light than the second wavelength of fluorescence of the remaining three bases when the modified bases are sequentially excited by the chosen electromagnetic radiation.

8. The method as described in claim 5, wherein the fluorescent dyes are separated from each base by attachment of a linker arm in order to assist in the synthesis and cleavage of the complementary strand of DNA or RNA.

9. A method for DNA and RNA nucleotide base sequencing comprising the steps of:

(a) isolating a single fragment of DNA or RNA;

(b) enzymatically synthesizing a strand of DNA or RNA complementary to the single fragment of DNA or RNA to be sequenced using nucleotide bases modified such that a chosen first base selected from the group consisting of the four bases found in DNA or RNA is modified by attachment of a first fluorescent dye which fluoresces at a first wavelength of light characteristic of the first modified base when excited using a chosen spectrum of electromagnetic radiation, and the remaining three bases found in DNA or RNA are each modified to have a reactive center selected from the group consisting of amino and sulfhydro groups;

(c) attaching said synthesized complementary strand to a microsphere and suspending said microsphere in a laminar flow fluid stream;

(d) sequentially cleaving the end base from the DNA or RNA fragment to form a train of modified bases in said stream;

(e) attaching a fluorescent dye to each reactive center such that the fluorescent dye fluoresces at a second wavelength of light characteristic of the three bases modified to have a reactive center when excited using the electromagnetic radiation;

(f) exciting each modified base in the train of modified bases with the chosen electromagnetic radiation; and (g) detecting the fluorescence at either the first wavelength of light or the second wavelength of light for each modified base in the train in sequential passage through a detector which detects the fluorescence from single molecules wherein said step of detecting provides information on the nucleotide sequence of said single fragment of DNA or RNA to be sequenced.

10. The method as described in claim 9, wherein said step of sequentially cleaving the end base from the DNA or RNA is achieved using exonuclease.

11. The method as described in claim 9, wherein said steps (a) through (g) are sequentially repeated two additional times using identical single fragments of DNA or RNA, whereby in each completed sequence of steps a different first base is chosen for modification such that the chosen first base fluoresces at a different first wavelength of light than the second wavelength of fluorescence of the remaining three bases when the modified bases are sequentially excited by the chosen electromagnetic radiation.

12. The method as described in claim 9, wherein the chosen first base and the remaining three types of bases are modified by attachment of fluorescent dyes which are separated from the base using a linker arm in order to assist in the synthesis and cleavage of the complementary strand of DNA or RNA.

13. A method for DNA and RNA nucleotide base sequencing comprising the steps of:

(a) isolating a single fragment of DNA or RNA;

(b) enzymatically synthesizing a strand of DNA or RNA complementary to the single fragment of DNA or RNA to be sequenced using nucleotide bases modified such that a chosen first base selected from the group consisting of the four bases found in DNA or RNA is modified to have a reactive center selected from the group consisting of amino and sulfhydro groups, and the remaining three bases found in DNA or RNA are each modified by attachment of a first fluorescent dye which fluoresces at a first wavelength of light characteristic of the remaining modified bases when excited using a chosen spectrum of electromagnetic radiation;

(c) attaching said synthesized complementary strand to a microsphere and suspending said microsphere in a laminar flow fluid stream;

(d) sequentially cleaving the end base from the DNA or RNA fragment to form a train of modified bases in said stream;

(e) attaching a fluorescent dye to each reactive center such that the fluorescent dye fluoresces at a second wavelength of light characteristic of the chosen first base when excited using the electromagnetic radiation;

(f) exciting each modified base in the train of modified bases with the chosen electromagnetic radiation; and (g) detecting the fluorescence at either the first wavelength of light or the second wavelength of light for each modified base in the train in sequential passage through a detector which detects the fluorescence from single molecules wherein said step of detecting provides information on the nucleotide sequence of said single fragment of DNA or RNA to be sequenced.

14. The method as described in claim 13, wherein said step of sequentially cleaving the end base from the DNA or RNA is achieved using exonuclease.

15. The method as described in claim 13, wherein said steps (a) through (g) are sequentially repeated two additional times using identical single fragments of DNA or RNA, whereby in each completed sequence of steps a different first base chosen for modification such that the chosen first base fluoresces at a different first wavelength of light than the second wavelength of fluorescence of the remaining three bases when the modified bases are sequentially excited by the chosen electromagnetic radiation.

16. The method as described in claim 13, wherein the chosen first base and the remaining three bases are modified by attachment of fluorescent dyes which are separated from the base using a linker arm in order to assist in the synthesis and cleavage of the complementary strand of DNA or RNA.

17. A method for DNA and RNA nucleotide base sequencing comprising the steps
 (a) isolating a single fragment of DNA and RNA;
 (b) enzymatically synthesizing a strand of DNA or RNA complementary to the single fragment of DNA or RNA to be sequenced using nucleotide bases modified such that a chosen first base type selected from the group consisting of the four bases found in DNA or RNA is modified by attachment of a first fluorescent dye which fluoresces at a first wavelength of light characteristic of the first modified base when excited using a chosen spectrum of electromagnetic radiation, and a second chosen base type selected from the bases found in DNA or RNA is modified by attachment of a second fluorescent dye which fluoresces at a second wavelength of light characteristic of the second modified base when excited using the chosen electromagnetic radiation;
 (c) attaching said synthesized complementary strand to a microsphere and suspending said microsphere in a laminar flow fluid stream
 (d) sequentially cleaving the end base from the DNA or RNA fragment to form a train of modified bases in said stream;
 (e) exciting each modified base in the train of modified bases with the chosen electromagnetic radiation; and
 (f) detecting the fluorescence at either the first wavelength of light or at the second wavelength of light for each modified base in the train in sequential passage through a detector which detects the fluorescence from single molecules wherein said step of detecting provides information on the nucleotide sequence of said single fragment of DNA or RNA to be sequenced.

18. The method as described in claim 17, wherein said step of sequentially cleaving the end base from the DNA or RNA is achieved using exonuclease.

19. The method as described in claim 17, wherein said steps (a) through (f) are sequentially repeated five additional times using identical single fragments of DNA or RNA, whereby in each completed sequence of steps a different combination of first base and second base are chosen for modification such that the chosen first base fluoresces at a different first wavelength of light than the second wavelength of fluorescence of the chosen second base when the modified bases are sequentially excited by the chosen electromagnetic radiation.

20. The method as described in claim 17, wherein the chosen first base and the remaining three bases are modified by attachment of fluorescent dyes which are separated from the base using a linker arm in order to assist in the synthesis and cleavage of the complementary strand of DNA or RNA.

21. A method for DNA and RNA nucleotide base sequencing comprising the steps of:
 (a) isolating a single fragment of DNA or RNA;
 (b) enzymatically synthesizing a strand of DNA or RNA complementary to the single fragment of DNA or RNA to be sequenced using nucleotide bases modified such that a chosen first base selected from the group consisting of the four bases found in DNA or RNA is modified to have a first reactive center selected from the group consisting of amino and sulfhydro groups, and a chosen second base selected from the group of four bases found in DNA or RNA is modified to have a second reactive center selected from the group consisting of amino and sulfhydro groups;
 (c) attaching said synthesized complementary strand to a microsphere and suspending said microsphere in a laminar flow fluid stream;
 (d) sequentially cleaving the end base from the DNA or RNA fragment to form a train of modified bases in said stream;
 (e) attaching a first fluorescent dye to each first reactive center and a second fluorescent dye to each second reactive center, such that the first fluorescent dye fluoresces at a first wavelength of light characteristic of the first modified base when excited using a chosen spectrum of electromagnetic radiation, and the second fluorescent dye fluoresces at a second wavelength of light characteristic of the second modified base when excited using the chosen electromagnetic radiation;
 (f) exciting each modified base in the train of modified bases with the chosen electromagnetic radiation; and
 (g) detecting the fluorescence at either the first wavelength of light or at the second wavelength of light for each modified base in the train in sequential passage through a detector which detects the fluorescence from single molecules wherein said step of detecting provides information on the nucleotide sequence of said single fragment of DNA or RNA to be sequenced.

22. The method as described in claim 21, wherein said step of sequentially cleaving the end base from the DNA or RNA is achieved using exonuclease.

23. The method as described in claim 21, wherein said steps (a) through (g) are sequentially repeated five additional times using identical single fragments of DNA or RNA, whereby in each completed sequence of steps a different combination first base and second base is chosen for modification such that the chosen first base fluoresces at a different first wavelength of light than the second wavelength of fluorescence of the second base when the modified bases are sequentially excited by the chosen electromagnetic radiation.

24. The method as described in claim 21, wherein the fluorescent dyes are separated from each base by attachment of a linker arm in order to assist in the synthesis and cleavage of the complementary strand of DNA or RNA.

25. A method for DNA and RNA nucleotide base sequencing comprising the steps of:
(a) isolating a single fragment of DNA or RNA;
(b) enzymatically synthesizing a strand of DNA or RNA complementary to the single fragment of DNA or RNA to be sequenced using nucleotide bases modified such that a chosen first base selected from the group consisting of the four bases found in DNA or RNA is modified by attachment of a first fluorescent dye which fluoresces at a first wavelength of light characteristic of the first modified base when excited using a chosen spectrum of electromagnetic radiation, and a chosen second base is modified to have a reactive center selected from the group consisting of amino and sulfhydro groups;
(c) attaching said synthesized complementary strand to a microsphere and suspending said microsphere in a laminar flow fluid stream;
(d) sequentially cleaving the end base from the DNA or RNA fragment to form a train of modified bases in said stream;
(e) attaching a fluorescent dye to each reactive center such that the fluorescent dye fluoresces at a second wavelength of light characteristic of the chosen second base modified to have a reactive center when excited using the electromagnetic radiation;
(f) exciting each modified base in the train of modified bases with the chosen electromagnetic radiation; and
(g) detecting the fluorescence at either the first wavelength of light or the second wavelength of light for each modified base in the train in sequential passage through a detector which detects the fluorescence from single molecules wherein said step of detecting provides information on the nucleotide sequence of said single fragment of DNA or RNA to be sequenced.

26. The method as described in claim 25, wherein said step of sequentially cleaving the end base from the DNA or RNA is achieved using exonuclease.

27. The method as described in claim 25, wherein said steps (a) through (g) are sequentially repeated five additional times using identical single fragments of DNA or RNA, whereby in each completed sequence of steps a different combination of first base and second base is chosen for modification such that the chosen first base fluoresces at a different first wavelength or light than the second wavelength of fluorescence of the chosen second base when the modified bases are sequentially excited by the chosen electromagnetic radiation.

28. The method as described in claim 25, wherein the chosen first base and the chosen second base are modified by attachment of fluorescent dyes which are separated from the base using a linker arm in order to assist in the synthesis and cleavage of the complementary strand of DNA or RNA.

29. A method for DNA and RNA nucleotide base sequencing comprising the steps of:
(a) isolating a single fragment of DNA or RNA;
(b) enzymatically synthesizing a strand of DNA or RNA complementary to the single fragment of DNA or RNA to be sequenced using nucleotide bases modified such that a chosen first base selected from the group consisting of the four bases found in DNA or RNA is modified to have a first reactive center selected from the group consisting of amino and sulfhydro groups, while the remaining three bases found in DNA or RNA are each modified to have a second reactive center selected from the group consisting of amino and sulfhydro groups;
(c) attaching a first fluorescent dye to each first reactive center and a second fluorescent dye to each second reactive center, such that the first fluorescent dye fluoresces at a first wavelength of light characteristic of the first modified base when excited using a chosen spectrum of electromagnetic radiation, and the second fluorescent dye fluoresces at a second wavelength of light characteristic of the remaining three types of bases found in DNA or RNA when excited using the chosen electromagnetic radiation;
(d) attaching said synthesized complementary strand to a microsphere and suspending said microsphere in a laminar flow fluid stream;
(e) sequentially cleaving the end base from the DNA or RNA fragment to form a train of modified bases in said stream;
(f) exciting each modified base in the train of modified bases with the chosen electromagnetic radiation; and
(g) detecting the fluorescence at either the first wavelength of light or at the second wavelength of light for each modified base in the train in sequential passage through a detector which detects the fluorescence from single molecules.

30. The method as described in claim 29, wherein said step of sequentially cleaving the end base from the DNA or RNA is achieved using exonuclease.

31. The method as described in claim 29, wherein said steps (a) through (g) are repeated two additional times using identical single fragments of DNA or RNA, whereby in each completed sequence of steps a different first base is chosen for modification such that the chosen first base fluoresces at a different first wavelength of light than the second wavelength of fluorescence of the remaining three bases when the modified bases are sequentially excited by the chosen electromagnetic radiation.

32. The method as described in claim 29, wherein the fluorescent dyes are separated from each base by attachment of a linker arm in order to assist in the synthesis and cleavage of the complementary strand of DNA or RNA.

33. A method for DNA and RNA nucleotide base sequencing comprising the steps of:
(a) isolating a single fragment of DNA or RNA;
(b) enzymatically synthesizing a strand of DNA or RNA complementary to the single fragment of DNA or RNA to be sequenced using nucleotide bases modified such that a chosen first base selected from the group consisting of the four bases found in DNA or RNA is modified by attachment of a first fluorescent dye which fluoresces at a first wavelength of light characteristic of the first modified base when excited using a chosen spectrum of electromagnetic radiation, and the remaining three bases found in DNA or RNA are each modified to have a reactive center selected from the group consisting of amino and sulfhydro groups;

(c) attaching a fluorescent dye to each reactive center such that the fluorescent dye fluoresces at a second wavelength of light characteristic of the three bases modified to have a reactive center when excited using the electromagnetic radiation;

(d) attaching said synthesized complementary strand to a microsphere and suspending said microsphere in a laminar flow fluid stream;

(e) sequentially cleaving the end base from the DNA or RNA fragment to form a train of modified bases in said stream;

(f) exciting each modified base in the train of modified bases with the chosen electromagnetic radiation; and (g) detecting the fluorescence at either the first wavelength of light or the second wavelength of light for each modified base in the train in sequential passage through a detector which detects the fluorescence from single molecules wherein said step of detecting provides information on the nucleotide sequence of said single fragment of DNA or RNA to be sequenced.

34. The method as described in claim 33, wherein said step of sequentially cleaving the end base from the DNA or RNA is achieved using exonuclease.

35. The method as described in claim 33, wherein said steps (a) through (g) are sequentially repeated two additional times using identical single fragments of DNA or RNA, whereby in each completed sequence of steps a different first base is chosen for modification such that the chosen first base fluoresces at a different first wavelength of light than the second wavelength of fluorescence of the remaining three bases when the modified bases are sequentially excited by the chosen electromagnetic radiation, 36. The method as described in claim 33, wherein the chosen first base and the remaining three bases are modified by attachment of fluorescent dyes which are separated from the base using a linker arm in order to assist in the synthesis and cleavage of the complementary strand of DNA or RNA.

37. A method for DNA and RNA nucleotide base sequencing comprising the steps of:

(a) isolating a single fragment of DNA or RNA;

(b) enzymatically synthesizing a strand of DNA or RNA complementary to the single fragment of DNA or RNA to be sequenced using nucleotide bases modified such that a chosen first base selected from the group consisting of the four bases found in DNA or RNA is modified to have a reactive center selected from the group consisting of amino and sulfhydro groups, and the remaining three bases found in DNA or RNA are each modified by attachment of a first fluorescent dye which fluoresces at a first wavelength of light characteristic of the remaining modified bases when excited using a chosen spectrum of electromagnetic radiation;

(c) attaching a fluorescent dye to each reactive center such that the fluorescent dye fluoresces at a second wavelength of light characteristic of the chosen first base when excited using the electromagnetic radiation;

(d) attaching said synthesized complementary strand to a microsphere and suspending said microsphere in a laminar flow fluid stream;

(e) sequentially cleaving the end base from the DNA or RNA fragment to form a train of modified bases in said stream;

(f) exciting each modified base in the train of modified bases with the chosen electromagnetic radiation; and (g) detecting the fluorescence at either the first wavelength of light or the second wavelength of light for each modified base in the train in sequential passage through a detector which detects the fluorescence from single molecules wherein said step of detecting provides information on the nucleotide sequence of said single fragment of DNA or RNA to be sequenced.

38. The method as described in claim 37, wherein said step of sequentially cleaving the end base from the DNA or RNA is achieved using exonuclease.

39. The method as described in claim 37, wherein said steps (a) through (g) are sequentially repeated two additional times using identical single fragments of DNA or RNA, whereby in each completed sequence of steps a different first base is chosen for modification such that the chosen first base fluoresces at a different first wavelength of light than the second wavelength of fluoresce has of the remaining three bases when the modified bases are sequentially excited by the chosen electromagnetic radiation.

40. The method as described in claim 37, wherein the chosen first base and the remaining three bases are modified by attachment of fluorescent dyes which are separated from the base using a linker arm in order to assist in the synthesis and cleavage of the complementary strand of DNA or RNA.

41. A method for DNA and RNA nucleotide base sequencing comprising the steps of:

(a) isolating a single fragment of DNA or RNA;

(b) enzymatically synthesizing a strand of DNA or RNA complementary to the single fragment of DNA or RNA to be sequenced using nucleotide bases modified such that a chosen first base selected from the group consisting of the four bases found in DNA or RNA is modified to have a first reactive center selected from the group consisting of amino and sulfhydro groups, and a chosen second base selected from the group of four bases found in DNA or RNA is modified to have a second reactive center selected from the group consisting of amino and sulfhydro groups;

(c) attaching a first fluorescent dye to each first reactive center and a second fluorescent dye to each second reactive center, such that the first fluorescent dye fluoresces at a first wavelength of light characteristic of the first modified base when excited using a chosen spectrum of electromagnetic radiation, and the second fluorescent dye fluoresces at a second wavelength of light characteristic of the second modified base when excited using the chosen electromagnetic radiation;

(d) attaching said synthesized complementary strand to a microsphere and suspending said microsphere in a laminar flow fluid stream;

(e) sequentially cleaving the end base from the DNA or RNA fragment to form a train of modified bases in said stream;

(f) exciting each modified base in the train of modified bases with the chosen electromagnetic radiation; and (g) detecting the fluorescence at either the first wavelength of light or at the second wavelength of light for each modified base in the train in sequential passage through a detector which detects the fluorescence from single molecules wherein said step of detecting provides information on the nucleotide sequence of said single fragment of DNA or RNA to be sequenced.

42. The method as described in claim 41, wherein said step of sequentially cleaving the end base from the DNA or RNA is achieved using exonuclease.

43. The method as described in claim 41, wherein said steps (a) through (g) are sequentially repeated five additional times using identical single fragments of DNA or RNA, whereby in each completed sequence of steps a different combination first base and second base is chosen for modification such that the chosen first base fluoresces at a different first wavelength of light than the second wavelength of fluorescence of the second base when the modified bases are sequentially excited by the chosen electromagnetic radiation.

44. The method as described in claim 41, wherein the fluorescent dyes are separated from each base by attachment of a linker am in order to assist in the synthesis and cleavage of the complementary strand of DNA or RNA.

45. A method for DNA and RNA nucleotide base sequencing comprising the steps of:
(a) isolating a single fragment of DNA or RNA;
(b) enzymatically synthesizing a strand of DNA or RNA complementary to the single fragment of DNA or RNA to be sequenced using nucleotide bases modified such that a chosen first base selected from the group consisting of the four bases found in DNA or RNA is modified by attachment of a first fluorescent dye which fluoresces at a first wavelength of light characteristic of the first modified base when excited using a chosen spectrum of electromagnetic radiation, and a chosen second base is modified to have a reactive center selected from the group consisting of amino and sulfhydro groups;
(c) attaching a fluorescent dye to each reactive center such that the fluorescent dye fluoresces at a second wavelength of light characteristic of the chosen second base type modified to have a reactive center when excited using the electromagnetic radiation;
(d) attaching said synthesized complementary strand to a microsphere and suspending said microsphere in a laminar flow fluid stream;
(e) sequentially cleaving the end base from the DNA or RNA fragment to form a train of modified bases in said stream;
(f) exciting each modified base in the train of modified bases with the chosen electromagnetic radiation; and
(g) detecting the fluorescence at either the first wavelength of light or the second wavelength of light for each modified base in the train in sequential passage through a detector which detects the fluorescence from single molecules wherein said step of detecting provides information on the nucleotide sequence of said single fragment of DNA or RNA to be sequenced.

46. The method as described in claim 45, wherein said step of sequentially cleaving the end base from the DNA or RNA is achieved using exonuclease.

47. The method as described in claim 45, wherein said steps (a) through (g) are sequentially repeated five additional times using identical single fragments of DNA or RNA, whereby in each completed sequence of steps a different combination of first base and second base is chosen for modification such that the chosen first base fluoresces at a different first wavelength of light than the second wavelength of fluorescence of the chosen second base when the modified bases are sequentially excited by the chosen electromagnetic radiation.

48. The method as described in claim 45, wherein the chosen first base and the chosen second base are modified using fluorescent dyes which are separated from the base using a linker arm in order to assist in the synthesis and cleavage of the complementary strand of DNA or RNA.

49. A method for DNA and RNA nucleotide base sequencing comprising the steps of:
(a) isolating a single fragment of DNA or RNA;
(b) enzymatically synthesizing a strand of DNA or RNA complementary to the single fragment of DNA or RNA to be sequenced using nucleotide bases modified such that a chosen first base selected from the group consisting of the four bases found in DNA or RNA is modified to have a first reactive center selected from the group consisting of amino and sulfhydro groups, and the remaining three bases found in DNA or RNA are each modified to have a second reactive center selected from the group consisting of amino and sulfhydro groups;
(c) attaching a fluorescent dye to each first reactive center such that the fluorescent dye fluoresces at a first wavelength of light characteristic of the chosen first base modified to have a first reactive center when excited using a chosen spectrum of electromagnetic radiation;
(d) attaching said synthesized complementary strand to a microsphere and suspending said microsphere in a laminar flow fluid stream;
(e) sequentially cleaving the end base from the DNA or RNA fragment to form a train of modified bases in said stream;
(f) attaching a fluorescent dye to each second reactive center such that the fluorescent dye fluoresces at a second wavelength of light characteristic of the three bases modified to have a second reactive center when excited using the electromagnetic radiation;
(g) exciting each modified base in the train of modified bases with the chosen electromagnetic radiation; and
(h) detecting the fluorescence at either the first wavelength of light or the second wavelength of light for each modified base in the train in sequential passage through a detector which detects the fluorescence from single molecules.

50. The method as described in claim 49, wherein said step of sequentially cleaving the end base from the DNA or RNA is achieved using exonuclease.

51. The method as described in claim 49, wherein said steps (a) through (h) are sequentially repeated two additional times using identical single fragments of DNA or RNA, whereby in each completed sequence of steps a different first base is chosen for modification such that the chosen first base fluoresces at a different first wavelength of light than the second wavelength of fluorescence of the remaining three bases when the modified bases are sequentially excited by the chosen electromagnetic radiation.

52. The method as described in claim 49, wherein the chosen first base and the remaining three bases are modified by attachment of fluorescent dyes which are separated from the base using a linker arm in order to assist in the synthesis add cleavage of the complementary strand of DNA or RNA.

53. A method for DNA and RNA nucleotide base sequencing comprising the steps of:
   (a) isolating a single fragment of DNA or RNA;
   (b) enzymatically synthesizing a strand of DNA or RNA complementary to the single fragment of DNA or RNA to be sequenced using nucleotide bases modified such that a chosen first base selected from the group consisting of the four bases found in DNA or RNA is modified to have a first reactive center selected from the group consisting of amino and sulfhydro groups, and the remaining three bases found in DNA or RNA are each modified to have a second reactive center selected from the group consisting of amino and sulfhydro groups;
   (c) attaching a fluorescent dye to each second reactive center such that the fluorescent dye fluoresces at a first wavelength of light characteristic of the three types of bases modified to have the second reactive center when excited using a chosen spectrum of electromagnetic radiation;
   (d) attaching said synthesized complementary strand to a microsphere and suspending said microsphere in a laminar flow fluid stream;
   (e) sequentially cleaving the end base from the DNA or RNA fragment to form a train of modified bases in said stream;
   (f) attaching a fluorescent dye to each first reactive center such that the fluorescent dye fluoresces at a second wavelength of light characteristic of the chosen first base when excited using a chosen spectrum of electromagnetic radiation using the electromagnetic radiation;
   (g) exciting each modified base in the train of modified bases with the chosen electromagnetic radiation; and
   (h) detecting the fluorescence at either the first wavelength of light or the second wavelength of light for each modified base in the train in sequential passage through a detector which detects the fluorescence from single molecules wherein said step of detecting provides information on the nucleotide sequence of said single fragment of DNA or RNA to be sequenced.

54. The method as described in claim 53, wherein said step of sequentially cleaving the end base from the DNA or RNA is achieved using exonuclease.

55. The method as described in claim 53, wherein said steps (a) through (h) are sequentially repeated two additional times using identical single fragments of DNA or RNA, whereby in each completed sequence of steps a different first base is chosen for modification such that the chosen first base fluoresces at a different first wavelength of light than the second wavelength of fluorescence of the remaining three bases when the modified bases are sequentially excited by the chosen electromagnetic radiation.

56. The method as described in claim 53, wherein the chosen first base and the remaining three bases are modified by attachment of fluorescent dyes which are separated from the base using a linker arm in order to assist in the synthesis and cleavage of the complementary strand of DNA or RNA.

57. A method for DNA and RNA nucleotide base sequencing comprising the steps of:
   (a) isolating a single fragment of DNA or RNA;
   (b) enzymatically synthesizing a strand of DNA or RNA complementary to the single fragment of DNA or RNA to be sequenced using nucleotide bases modified such that a chosen first base selected from the group consisting of the four bases found in DNA or RNA is modified to have a first reactive center selected from the group consisting of amino and sulfhydro groups, and a chosen second base is modified to have a second reactive center selected from the group consisting of amino and sulfhydro groups;
   (c) attaching a fluorescent 6lye to each first reactive center such that the fluorescent dye fluoresces at a first wavelength of light characteristic of the chosen first base modified to have a first reactive center when excited using a chosen spectrum of electromagnetic radiation
   (d) attaching said synthesized complementary strand to a microsphere and suspending said microsphere in a laminar flow fluid stream;
   (e) sequentially cleaving the end base from the DNA or RNA fragment to form a train of modified bases in said stream;
   (f) attaching a fluorescent dye to each second reactive center such that the fluorescent dye fluoresces at a second wavelength of light characteristic of the chosen second base modified to have a second reactive center when excited using the electromagnetic radiation;
   (g) exciting each modified base in the train of modified bases with the chosen electromagnetic radiation; and
   (h) detecting the fluorescence at either the first wavelength of light or the second wavelength of light for each modified base in the train in sequential passage through a detector which detects the fluorescence from single molecules wherein said step of detecting provides information on the nucleotide sequence of said single fragment of DNA or RNA to be sequenced.

58. The method as described in claim 57, wherein said step of sequentially cleaving the end base from the DNA or RNA is achieved using exonuclease.

59. The method as described in claim 57, wherein said steps (a) through (h) are sequentially repeated five additional times using identical single fragments of DNA or RNA, whereby in each completed sequence of steps a different combination of first base and second base is chosen for modification such that the chosen first base fluoresces at a different first wavelength of light than the second wavelength of fluorescence of the chosen second base when the modified bases are sequentially excited by the chosen electromagnetic radiation.

60. The method as described in claim 57, wherein the chosen first base and the chosen second base are modified by attachment of fluorescent dyes which are separated from the base using a linker arm in order to assist in the synthesis and cleavage of the complementary strand of DNA or RNA.

* * * * *